United States Patent
DiFoggio

(10) Patent No.: US 7,219,541 B2
(45) Date of Patent: May 22, 2007

(54) METHOD AND APPARATUS FOR DOWNHOLE FLUID ANALYSIS FOR RESERVOIR FLUID CHARACTERIZATION

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/082,424

(22) Filed: Mar. 17, 2005

(65) Prior Publication Data
US 2005/0205256 A1    Sep. 22, 2005

Related U.S. Application Data

(60) Provisional application No. 60/553,921, filed on Mar. 17, 2004.

(51) Int. Cl.
*E21B 49/00* (2006.01)

(52) U.S. Cl. .................. 73/152.17; 73/152.25

(58) Field of Classification Search ........... 73/152.02, 73/152.03, 152.04, 152.08, 152.54, 152.55, 73/19.09, 19.12, 19.1; 250/253, 254, 255, 250/256, 268
See application file for complete search history.

(56) References Cited

U.S. PATENT DOCUMENTS

| | | | |
|---|---|---|---|
| 3,859,851 A * | 1/1975 | Urbanosky | 73/152.24 |
| 3,929,003 A * | 12/1975 | LLewellyn | 73/61.72 |
| 4,833,915 A | 5/1989 | Radd et al. | |
| 6,167,965 B1 * | 1/2001 | Bearden et al. | 166/250.15 |
| 6,223,822 B1 * | 5/2001 | Jones | 166/250.05 |
| 6,661,000 B2 * | 12/2003 | Smith et al. | 250/282 |
| 6,670,605 B1 * | 12/2003 | Storm et al. | 250/255 |
| 6,834,536 B2 * | 12/2004 | Kempe | 73/61.41 |
| 2003/0033866 A1 * | 2/2003 | Diakonov et al. | 73/152.55 |
| 2004/0104341 A1 * | 6/2004 | Betancourt et al. | 250/255 |

* cited by examiner

*Primary Examiner*—Robert Raevis
(74) *Attorney, Agent, or Firm*—Madan, Mossman & Sriram, P.C.

(57) ABSTRACT

A formation fluid sample is exposed to a rigidly-supported semi-permeable membrane such as silicone rubber to permit diffusion of gases and vapors from the formation fluid into a vacuum chamber, while at the same time, blocking the passage of any liquids. The membrane-transmitted gas is analyzed in the vacuum chamber by a residual gas analyzer. An ion pump or sorbent is associated with the evacuated chamber to maintain the vacuum. The ion pump or sorbent removes gases and vapors from the chamber that diffuse into the chamber from the reservoir sample that is on the opposite side of the semi-permeable membrane.

30 Claims, 4 Drawing Sheets

```
┌─────────────────────────────────────┐
│ CAPTURE FORMATION FLUID SAMPLE      │──401
└─────────────────────────────────────┘
                  │
                  ▼
┌─────────────────────────────────────┐
│ EVACUATE GAS ANALYSIS CHAMBER       │──403
└─────────────────────────────────────┘
                  │
                  ▼
┌─────────────────────────────────────┐
│ DIFFUSE GAS FROM FORMATION FLUID    │──405
└─────────────────────────────────────┘
                  │
                  ▼
┌─────────────────────────────────────┐
│ MONITOR GAS TO IDENTIFY, QUANTIFY   │──407
│ AND DISTINGUISH GASES               │
└─────────────────────────────────────┘
                  │
                  ▼
┌─────────────────────────────────────┐
│ PUMP DIFFUSED GASES FROM            │──409
│ EVACUATED CHAMBER                   │
└─────────────────────────────────────┘
```

*Fig. 5*

| GAS | SSP-M100 | GAS | SSP-M100 | GAS | SSP-M213 |
|---|---|---|---|---|---|
| $H_2$ | 55 | $n\text{-}C_5H_{12}$ | 1670 | $CO_2$ | 97 |
| He | 30 | $n\text{-}C_6H_{14}$ | 785 | $H_2$ | 21 |
| $NH_3$ | 500 | $n\text{-}C_8H_{18}$ | 715 | $O_2$ | 16 |
| $H_2O$ | 3000 | $n\text{-}C_{10}H_{22}$ | 360 | $N_2$ | 7 |
| CO | 30 | HCHO | 925 | | |
| $N_2$ | 25 | $CH_3OH$ | 1160 | | |
| NO | 50 | $COCL_2$ | 1250 | | |
| $O_2$ | 50 | ACETONE | 490 | | |
| $H_2S$ | 840 | PYRIDINE | 1595 | | |
| Ar | 50 | BENZENE | 900 | | |
| $CO_2$ | 270 | PHENOL | 1750 | | |
| $N_2O$ | 385 | TOLUENE | 760 | | |
| $NO_2$ | 635 | Xe | 171 | | |
| $SO_2$ | 1250 | $CCl_4$ | 5835 | | |
| $CS_2$ | 7500 | $CH_2O$ | 925 | | |
| $CH_4$ | 80 | FREON 11 | 1290 | | |
| $C_2H_6$ | 210 | FREON 12 | 107 | | |
| $C_2H_4$ | 115 | FREON 22 | 382 | | |
| $C_2H_2$ | 2200 | FREON 114 | 211 | | |
| $C_3H_8$ | 340 | FREON 115 | 51 | | |
| $n\text{-}C_4H_{10}$ | 750 | | | | |

*Fig. 6*

METHOD AND APPARATUS FOR DOWNHOLE FLUID ANALYSIS FOR RESERVOIR FLUID CHARACTERIZATION

CROSS REFERENCE TO RELATED APPLICATIONS

This patent application claims priority from U.S. provisional patent application No. 60/553,921 entitled A Method and Apparatus for Downhole Fluid Analysis for Reservoir Fluid Characterization by Rocco DiFoggio, filed on Mar. 17, 2004 which is incorporated herein by reference in its entirety.

BACKGROUND OF THE INVENTION

1. Field of the Invention

The present invention relates generally to downhole reservoir characterization and in particular to a method and apparatus for real time identification of gases diffused out of a formation fluid sample. Formation fluid samples are obtained and gases are allowed to diffuse from these fluid samples through a semi-permeable membrane into an evacuated chamber. The gases are analyzed in the evacuated chamber by a mass spectrometer or residual gas analyzer (RGA) and a processor which identifies and distinguishes between gases such as $C_1$–$C_5$, $H_2S$, $CO_2$, $N_2$ and other gases or vapors present in a downhole reservoir fluid sample.

2. Summary of the Related Art

To obtain hydrocarbons such as oil and gas, boreholes are drilled into the earth by rotating a drill bit attached at to the end of a drill string. Modern directional drilling systems generally employ a drill string having a bottom hole assembly (BHA) and a drill bit at an end thereof that is rotated by a drill motor (mud motor) and/or by rotating the drill string. A number of downhole devices placed in close proximity to the drill bit measure certain downhole operating parameters associated with the drill string. Such devices typically include sensors for measuring downhole temperature and pressure, azimuth and inclination measuring devices and a resistivity-measuring device to determine the presence of hydrocarbons and water. Additional downhole instruments, known as logging-while-drilling (LWD) tools, are frequently attached to the drill string to determine the formation geology and formation fluid conditions during the drilling operations.

Commercial development of hydrocarbon fields requires significant amounts of capital. Before field development begins, operators desire to have as much data as possible regarding the nature of the hydrocarbon formation, in order to evaluate the reservoir for commercial viability. Despite the advances in data acquisition during drilling using the MWD systems and wire line analysis applications, it is often necessary to conduct further testing of the hydrocarbon reservoirs in order to obtain additional data. Therefore, after the well has been drilled, the hydrocarbon zones are often tested with other test equipment such as wire line tools, which are used to further analyze and monitor the formation.

One type of post-drilling test involves producing fluid from the reservoir and collecting such fluid samples downhole in tanks for transport to surface laboratories where Pressure-Volume-Temperature (PVT) studies and fluid properties such as density, viscosity and composition are measured. Also, one can measure the downhole fluid pressure at several depths and, from this pressure gradient, calculate the fluid's density.

Fluid samples extracted downhole are typically analyzed weeks to months later in a surface laboratory to identify and quantify gases present in the fluid. It is time consuming to retrieve fluid samples downhole and send them to a surface lab for analysis of gas content Moreover, surface analysis requires removal of the fluid sample and the tool from the borehole for testing the sample before additional exploration and/or production activities occur. Thus, there is a need for a real-time downhole method and apparatus for detection, distinction and quantification of gases in the formation.

SUMMARY OF THE INVENTION

The present invention provides a method and apparatus for real-time downhole detection, distinction and quantification of gases such as $C_1$–$C_5$, $H_2S$, $CO_2$, $N_2$ and other gases and vapors present in a formation fluid sample. The present invention can detect and analyze vapors associated with oil-based drilling fluid and therefore provide a real-time estimate of the percent contamination of the sample by drilling fluid filtrate.

The present invention exposes downhole high-temperature and high-pressure formation fluids to a semi-permeable membrane, which blocks liquids but allows passage of certain gases and vapors. This membrane is mechanically supported by a rigid but porous and permeable structure such as a sintered metal filter followed by a metal plate having some holes in it such that the membrane is capable of withstanding the pressure difference between a vacuum and downhole pressures. The semi-permeable membrane is made of a material such as silicone rubber, which permits the diffusion of gases and certain vapors from the formation fluid sample through the membrane and into a vacuum chamber adjacent the semi-permeable membrane.

The vacuum chamber forms a gas analysis chamber containing a residual gas analyzer (RGA). The RGA is a comparatively low resolution mass spectrometer such as those often used on high vacuum systems. A formation fluid sample is captured in a downhole tool and filtered by a semi-permeable membrane such as silicone rubber to permit diffusion of gases from the formation fluid into a vacuum chamber or gas analysis. The gases diffuse out of the formation fluid and analyzed by a residual gas analyzer (RGA) situated in the evacuated portion of the gas analysis chamber.

An ion pump is associated with the evacuated gas analysis chamber to maintain a vacuum in the chamber. The ion pump removes gases, which have diffused from the formation fluid sample into the evacuated chamber on the opposite side of the semi-permeable membrane filter. Alternatively, in place of an ion pump, activated charcoal or some other sorbent could be used to prevent the gases that have diffused into the vacuum from lingering there too long and interfering with the measurement of subsequent gases that have evolved or diffused from a subsequent sample.

In one aspect of the invention a method for estimating a property of a fluid downhole is provided comprising, exposing the fluid to a mass spectrometer; observing a response from the mass spectrometer; and estimating the property of the downhole fluid from the response. In another aspect of the invention the response is an intensity of a charge to mass ratio. In another aspect of the invention the response is a portion of a fragmentation pattern. In another aspect of the invention the method further comprises separating a gas from the fluid. In another aspect of the invention the separating further comprises diffusing the gas from the fluid. In another aspect of the invention the diffusing uses a semi-permeable membrane wherein the semi-permeable membrane admits a subset of the gas. In another aspect of the invention the diffusing further comprises selecting one of a plurality of membranes for diffusion of the gas. In another aspect of the invention each of the plurality of membranes is a different thickness. In another aspect of the invention the plurality of membranes is a different composition having an affinity for a different gas.

In yet another aspect of the invention an apparatus is provided for estimating a property of a fluid downhole comprising a mass spectrometer in fluid communication with the fluid; and a processor in communication with the mass spectrometer that estimates the property of the fluid. In another aspect of the invention the processor estimates the property of the fluid from a fragmentation pattern for the fluid. In another aspect of the invention the processor estimates the property of the fluid from an atomic mass unit (AMU) for the fluid. In another aspect of the invention the apparatus further comprises a separator exposed to the fluid. In another aspect of the invention the separator is a capillary tube. In another aspect of the invention the apparatus further comprises a membrane within the separator; and a gas chamber in communication with the separator and the mass spectrometer. In another aspect of the invention the membrane comprises a plurality of membranes. In another aspect of the invention the apparatus further comprises a valve for selecting at least one membrane from the plurality of membranes for diffusion of the gas. In another aspect of the invention each of the plurality of membranes has a different thickness from other membranes of the plurality of membranes. In another aspect of the invention each of the plurality of membranes has a different composition having a transmissiveness for a different gas from other membranes of the plurality of membranes. In another aspect of the invention the gas comprises a vapor.

BRIEF DESCRIPTION OF THE FIGURES

The novel features of this invention, as well as the invention itself, will be best understood from the attached drawings, taken along with the following description, in which similar reference characters refer to similar parts, and in which:

FIG. 5 is a flow chart of functions performed in an example of the present invention;

FIG. 6 is a table showing some examples of gas diffusion rates through a suitable semi-permeable membrane for use with the present invention;

DETAILED DESCRIPTION OF THE INVENTION

Figure 1:
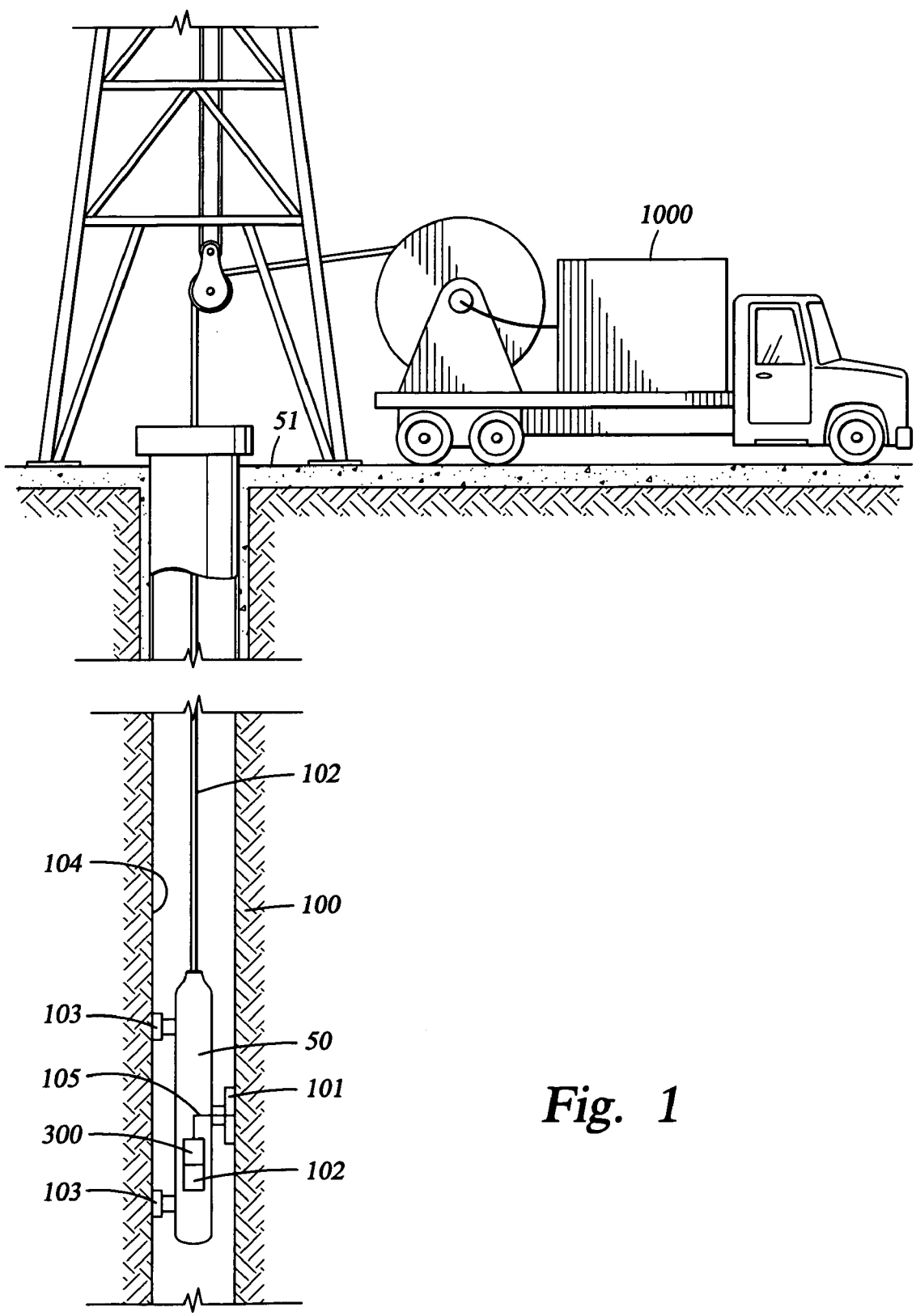
FIG. 1 is an illustration of an exemplary embodiment of the present invention as deployed in a borehole from a wire line.

The present invention provides a method and apparatus for real-time downhole detection, classification and quantification of gases trapped in a representative formation fluid sample. Gases such as $C_1$–$C_5$, $H_2S$, $CO_2$, $N_2$ and other gases and vapors present in a formation fluid sample are quantified by the present invention. The present invention exposes downhole high-temperature high-pressure formation fluid to a semi-permeable membrane such as silicone rubber to permit diffusion of gases from the formation fluid sample into a vacuum chamber containing a residual gas analyzer (RGA). The RGA is a relatively low-resolution mass spectrometer designed for use with high vacuum systems. Higher resolution mass spectrometers can also be used. The RGA is chosen because of its small size and because it is designed for use with high vacuum systems that are typically "baked out", at 250–300° C. Therefore, many RGA sensors are designed to survive (non-operationally) and operate up to 150° C., and are often designed to operate at "bake out" temperatures, provided that the RGA control electronics and processor remain at room temperature. The present invention provides high temperature RGA electronic control circuits, which can survive the downhole temperatures. Sorption cooling units are optionally provided adjacent the RGA electronics to enable the RGA electronic control circuits to survive and operate at elevated downhole temperatures.

The present invention analyzes high-temperature, high-pressure reservoir fluids by extracting and submitting a gaseous fraction of a formation fluid sample to the residual gas analyzer (RGA) and processor. A formation fluid sample is captured and filtered by a semi-permeable membrane, such as silicone rubber to permit diffusion of gases from the formation fluid sample into an evacuated gas analysis chamber. The diffused gas is analyzed by a residual gas analyzer (RGA) situated in the evacuated gas analysis chamber opposite the formation fluid chamber on the other side of the semi-permeable membrane. An ion pump (or in alternative embodiments sublimation or other pumps) is associated with the evacuated gas analysis chamber after it is initially evacuated (rough pumped) to help establish and to maintain a vacuum in the chamber. The ion pump removes gases from the evacuated chamber, which have diffused into the evacuated chamber from the formation fluid sample located on the opposite side of the semi-permeable membrane filter.

To distinguish between the gases with close AMU's the following functions are performed in the current example of the invention. The first function is to evacuate a vacuum chamber containing a RGA and processor to analyze gases. The vacuum chamber also is provided with an ion pump to maintain the vacuum. A semi-permeable membrane (such as silicone rubber) is placed at the inlet to the vacuum chamber to allow gases to diffuse into the vacuum chamber, while at the same time preventing liquids from entering the evacuated chamber. The gas analysis system is then calibrated for the diffusion rates of selected gases through the membrane at temperature and pressure, the fragmentation patterns of the selected gases, and for the sensitivity of the RGA to the selected gases.

Turning now to FIG. 1, FIG. 1 illustrates an example of the current invention deployed from a wire line 102 in a borehole 104 drilled in a formation 100. An extensible probe 101 extracts fluid from the formation 100. The extracted formation fluid flow through flow line 105 where the gas analysis chamber 300 of the present invention determines the gas content of the formation fluid sample. Stablizers 103 hold the tool 50 and extensible probe 101 in place during extraction of a formation fluid sample. The results of the gas analysis performed by the RGA and processor 102, can be acted on by processor 102 or the RGA analysis results can be sent to the surface 51 to acted on by the surface processor and control unit 1000.

Figure 2:
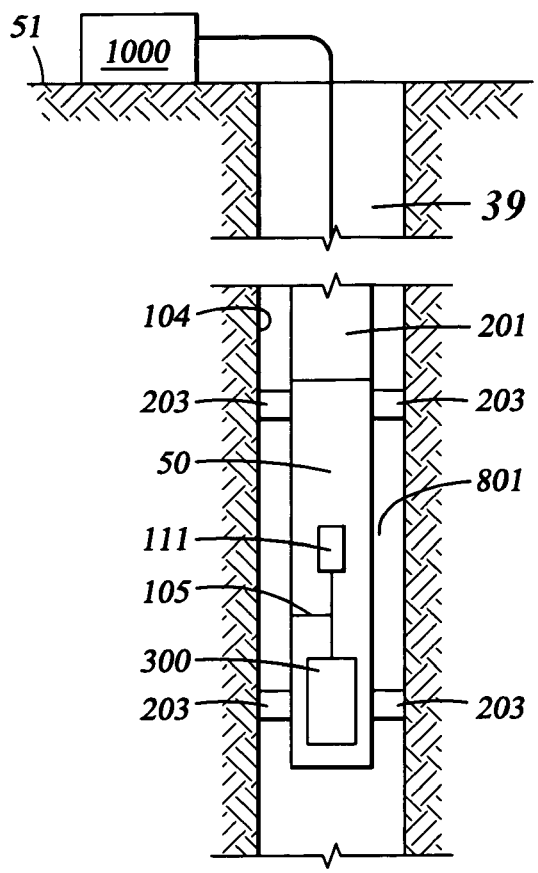
FIG. 2 is an illustration of an exemplary embodiment of the present invention as deployed in a borehole from a drill string.

Turning now to FIG. 2, another example of the current invention is shown deployed from a drill string 201. Straddle packers 203 hold the tool 50 in place during the entry of fluid through flow path 105 to the gas analysis chamber 300 of the present invention. The fluid can come from the annulus 39 between the tool 50 and the well bore 104 or from the formation 100. Fluid can be routed to the sample tank 111 or back to the well bore annulus 39 as desired based on the results of the density determination performed by the present invention 300. The results of the RGA gas analysis are acted on by the processor 102, or the results can be sent to the surface 51 to be acted on by surface processor and control 1000.

Figure 3:
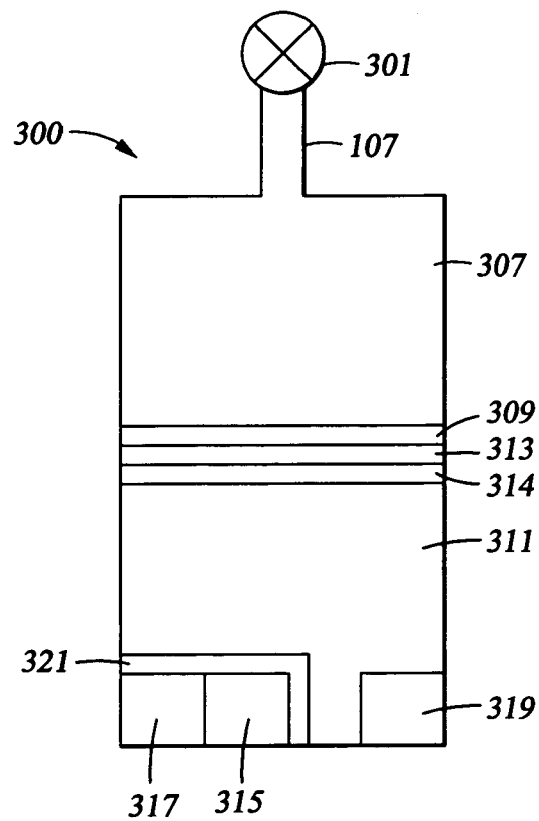
FIG. 3 is an illustration of the components comprising the current example of the invention.

Turning now to FIG. 3, a more detailed schematic of the present invention is shown. An RGA mass spectrometer 317, ion pump 319, semi-permeable membrane 309, fluid containment chamber 307 and processor 315 are shown in schematic form in FIG. 3. A sorption-cooling unit 321 is provided to maintain processor and RGA control electronics within their operating and/or survival temperature range. The formation fluid containment chamber 307 is separated from the evacuated gas analysis chamber 311 by the semi-permeable membrane 309. Thus, the formation fluid containment chamber 307 is positioned on one side of the semi-permeable membrane 309 and an evacuated gas analysis chamber 311 on the other side of the semi-permeable membrane 309. The gases trapped in the captured formation fluid sample diffuse across the semi-permeable membrane into the evacuated gas analysis chamber for analysis.

Figure 4:
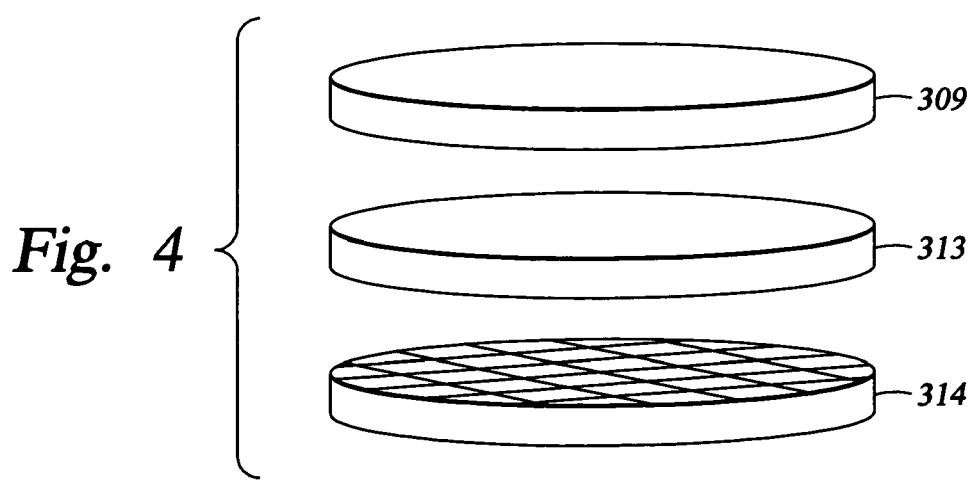
FIG. 4 illustrates the semi-permeable membrane, sintered metal filter and metal plate with small hole having scoring of fact of plate between the holes.

Formation fluid is extracted from the formation 100 and enters into the fluid containment chamber 307 via flow line 107 and valve 301. Gases diffuse from the formation fluid on the fluid side of the semi-permeable membrane, through the semi-permeable membrane and into the evacuated chamber 311. The gas analysis module equipment, RGA 317 and processor/control electronics 315 are located in the evacuated gas analysis chamber 311. The gas is exposed to and analyzed by the mass spectrometer (RGA) 317 and processor 102. The processor 102 and RGA electronics controls and conducts the RGA analysis. The processor 102 reports the analytical results to the surface via the wire line of other means of downhole communication. The processor 102 can act on the analysis results without reporting the results to the surface. FIG. 4 illustrates the semi-permeable membrane 309, sintered metal filter 313 and metal plate 314 with small hole having scoring of a face of the plate between the holes.

Turning now to FIG. 5, an example illustrating some of the functions performed by the present invention is illustrated. As shown in block 401, the present invention captures a formation fluid sample from the formation. The formation fluid enters the tool 50 via a flow line in fluid communication with the formation. In block 403, the gas analysis module chamber is evacuated. The evacuation of the gas analysis module enables gases trapped in the formation fluid sample to diffuse into the evacuated chamber through the semi-permeable membrane. In block 405 the semi-permeable membrane between the fluid and the evacuated chamber allows gases from the fluid to diffuse through the semi-permeable membrane into an evacuated gas analysis chamber. In block 407, the mass spectrometer (RGA) and processor of the present invention monitors the gases to detect, identify and quantify the gases and distinguish between them. In block 409, the ion pump removes diffused gases from the evacuated side of the chamber to maintain the vacuum.

Gas molecules can be distinguished from each other by the difference in their masses or by differences in the masses of the fragments into which they break when ionized. Expressed in atomic mass units (AMU), the unfragmented masses of some common gases are: $H_2$ (hydrogen) AMU=2.02, He (helium_3) AMU=3.00, $He_4$(helium_4) AMU=40.00, Ne (neon 20.18, Ar (argon) AMU=39.95, Kr (krypton) AMU=83.80, Xe (xenon) AMU=131.30, O2 (oxygen) AMU=32.00, N2 (nitrogen) AMU=28.01, $CO_2$ (carbon dioxide) AMU=44.01, $H_2S$ (hydrogen sulfide) AMU=34.08, SO2 (sulfur dioxide) AMU=64.06, $CH_4$ (methane) AMU=16.04, $C_2H_6$ (ethane) AMU=30.07, $C_3H_8$ (propane) AMU=44.10, C4H10 (butane) AMU=58.12, $C_5H_{12}$ (pentane) AMU=72.15. Interferences can occur between the masses of fragments created from these different gases during the ionization process in the mass spectrometer. These interferences can be resolved using matrix inversion techniques, chemometrics, or by monitoring a mass channel at which the corresponding mass fragment is known to come from only one species of gas or vapor.

Typically, a residual gas analyzer can only resolve a difference in mass of 1 AMU. Thus, an RGA would encounter difficulty distinguishing carbon dioxide (44.01) from propane (44.10). To distinguish between these two gases, in the current example of the present invention, the method and apparatus of the present invention examines the differences in their "fragmentation" (or "cracking") patterns. The fragmentation pattern is the pattern of smaller molecules into which the larger molecule is often broken during ionization in a mass spectrometer. Thus, depending on the fragmentation pattern discerned by the RGA and processor, the gases diffused from a formation fluid sample are detected and quantified.

Suitable semi-permeable membranes, residual gas analyzers and vacuum pumps are commercially available and suitable for use with the present invention are discussed herein. Furthermore, membranes can be specially designed to be selective to the transmission of one gas instead of transmitting many gases as silicone membranes do. In her research prospectus, (http://www.psrc.usm.edu/mauritz/diffuse.html ), Sandra Young of the School of Polymers at The University of Southern Mississippi, states:

Aromatic polyimides that contain —C(CF3)2— groups tend to have higher preference for CO2 relative to CH4. Introduction of —C(CF3)2— groups is believed to increase chain stiffness which reduces intrasegmental mobility, and reduce and limit the degree of chain packing by increasing the free volume, serving as molecular spacers and chain stiffeners in the polymer (Stern, S. A. J. Membrane Sci., 1994, 94, 1–65 and Kim, T. H.; Koros, W. J.; Husk, G. R.; O'Brien, K. C. J. Membrane Sci., 1988, 37, 45–62).

Polysulfones have been used for years as perm-selective membranes, starting in 1977 when Monsanto utilized asymmetric hollow fiber coated with a thin layer of silicone rubber for H2 separations. Asymmetric cellulose acetate membranes are used for the removal of CO2 and H2S from natural gas. CO2 and H2S have high solubility in cellulose acetate which induces pseudo-plasticization, causing the polymer to swell with disruption of the polymer matrix which increases the mobility of the polymer chains. In the area of rubbery polymers, the only systems currently under investigation are the poly(organosiloxanes). Poly(organosiloxanes) have been studied in detail because of the vast utility of polydimethylsiloxane (PDMS) as a preformed membrane that can then be used as a template for IPN formation in gas or liquid separation processes. PDMS possesses one of the greatest permeability coefficients of any polymer, due to its large free volume, and low selectivity. Through copolymerization, properties have the potential to be tailored to suit specific separation needs. Porosity control in materials used for separation processes is essential due to the potential variability of gases or liquids through the membrane. Sol-gel polymerizations can be manipulated to adjust the shrinkage of a network for the development of controlled porosity inorganic materials.

John J. Pellegrino of National Institute of Standards and Technology states: http://membranes.nist.gov/publication_abstracts/Pell_Ko_Nass_Eine.html CO2 and H2S can be selectively separated from each other and from non-polar gases, such as H2, CO and CH4 using chemically reactive carriers immobilized in a membrane phase. Ion-exchange membranes made from polyperfluorosulfonic acid (PFSA) have been modified to form a gel for use as the support for the solvent and carrier. The membrane contains hydrophilic regions into which a solvent, containing the desired chemical complexing agent, may be imbibed. In experiments performed at ambient conditions selectivities for CO2 versus H2 are 20 to 30 with CO2 permeabilities of 1000–2000 barrer. Higher selectivities and H2S permeabilities are obtained for the H2S—H2 separation. Our studies include characterization of this membrane with a variety of amine carriers and polar solvents at ambient temperatures and pressure. This paper presents a summary of the acid gas permeation rates and selectivities for the acid gases versus H2 and CO. Preliminary economic evaluations indicate that composite membranes with PFSA coated films 5 to 1 µm thick, would have capital costs lower than standard amine-absorber technology.

Figure 7:
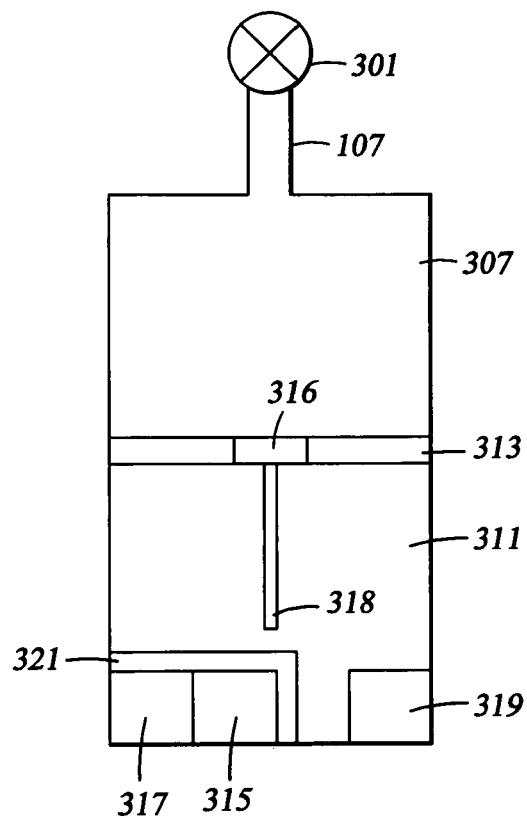
FIG. 7 illustrates an alternative embodiment having a filter and capillary tube input.
Figure 8:
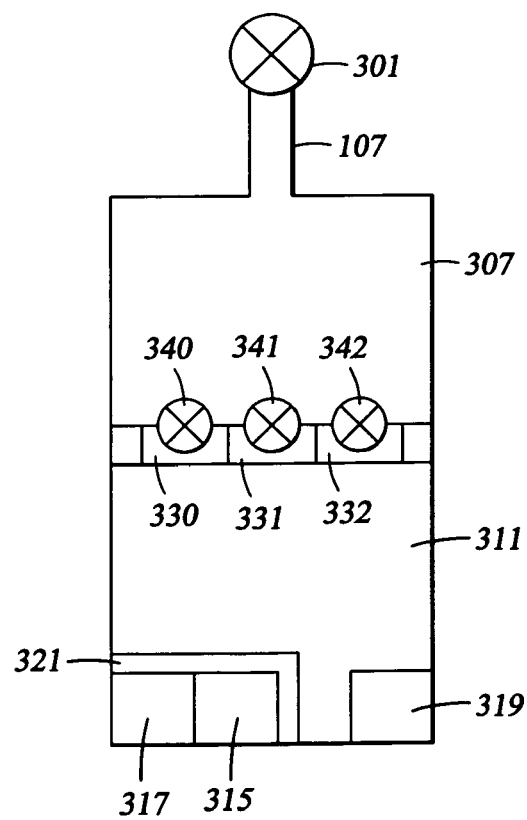
FIG. 8 illustrates a system with valves leading to multiple inlets each having a different membrane thickness, which is provided in an alternative embodiment.

FIG. 6 is a tabular listing and specification for some gases through a representative semi-permeable membrane, which is suitable for use with the present invention. The specifications for some small commercially available residual gas analyzers and small ion pumps are discussed below. FIG. 7 illustrates an alternative embodiment having a filter 316 and capillary tube 318 input to evacuated chamber 311. There is typically a tradeoff between the speed of response to gases in a fluid and the thickness of the semi-permeable membrane. FIG. 8 illustrates a system with valves 340, 341 and 342, leading to multiple inlets respectively each having a different composition semi-permeable membrane (e.g., Dimethyl Silicone Membrane or Silicone Polycarbonate Membrane) and/or different thickness, 330, 331 and 332 respectively which is provided in an alternative embodiment. For example, membrane 330 is 10 microns thick, 331 is 20 microns thick and 332 is 30 microns thick. Each membrane can also be of different composition having an affinity for a different gas. Thus, each valve 340, 341 and 342 can be opened one at a time and a different gas diffused through each membrane. The ion pump 319 removes the diffused gas and the valve is closed and another opened to let a different gas diffuse to vacuum chamber 311.

A suitable mass spectrometer for use with the present invention is available from Horiba Instruments Ltd., Laboratory, Unit 1, Ruskin Leisure Centre, Ruskin Drive, St. Helens, UK WA 10 6RP, Tel: 44(0) 1744 454 598 Fax: 44(0) 1744 454 599 or Extorr, Inc. 307 Columbia Road, New Kensington, PA 15068, USA Tel 1 724 337 3000 or INFINICON, INC., Two Technology Place, East Syracuse, NY 13057, USA Tel: 1 315–434 1100. A suitable ion pump is commercially available from Varian, Inc. 3120 Hansen Way, Palo Alto, Calif. 94304–1030, USA Tel: 1 650 213 8000.

In another embodiment of the present invention, the method of the present invention is implemented as a set computer executable of instructions on a computer readable medium, comprising ROM, RAM, CD ROM, Flash or any other computer readable medium, now known or unknown that when executed cause a computer to implement the method of the present invention.

While the foregoing disclosure is directed to the preferred embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated.

What is claimed is:

1. A method for estimating a property of fluid downhole, comprising:
    passing the fluid through a filter having a permeable membrane and a porous filter to separate at least one of gas and vapor to form a separated fluid; and
    analyzing the separated fluid downhole to estimate the property of the separated fluid.

2. The method of claim 1, wherein the filter further includes a rigid support for the porous filter.

3. The method of claim 1, wherein analyzing the separated fluid comprises:
    exposing the separated fluid to a mass spectrometer;
    observing a response from the mass spectrometer; and
    estimating the property of the separated fluid from the observed response.

4. The method of claim 3, wherein the response is one of (i) an intensity of a charge to mass ratio; and (ii) a portion of a fragmentation pattern.

5. The method of claim 1, wherein passing the fluid further comprises controlling the fluid by a valve.

6. The method of claim 1, wherein the permeable membrane is composed of a plurality of permeable membranes, each such membrane having a thickness thickness selected to allow passage of a selected fluid therethrough.

7. The method of claim 1 further comprising retrieving the fluid downhole into a first section of a chamber and collecting the separated fluid into a second section of the chamber.

8. The method of claim 7 further comprising evacuating the second section of the chamber.

9. The method of claim 8, wherein evacuating the second section of the chamber includes evacuating using an ion pump.

10. The method of claim 1 wherein the permeable membrane is composed of a plurality of permeable membranes, each such membrane having an affinity for one of (i) a different gas, and (ii) a different vapor.

11. An apparatus for estimating a property of fluid downhole, comprising:
    a filter having a permeable membrane and a porous filter to separate at least one of gas and vapor to form a separated fluid; and
    a processor analyzing the separated fluid downhole to estimate the property of the separated fluid.

12. The apparatus of claim 11, further comprising a rigid support for the filter.

13. The apparatus of claim 11, further comprising:
a mass spectrometer exposed to the separated fluid; and
wherein the processor estimates the property of the separated fluid by observing a response from the mass spectrometer.

14. The apparatus of claim 13, wherein the response is one of (i) an intensity of a charge to mass ratio; and (ii) a portion of a fragmentation pattern.

15. The apparatus of claim 11, further comprising a valve that controls passage of the fluid through the filter.

16. The apparatus of claim 11, wherein the permeable membrane comprises a plurality of permeable membranes, each such membrane having a thickness selected to allow passage of a selected fluid therethrough.

17. The apparatus of claim 11 further comprising a chamber having a first section retrieving the fluid downhole, and a second section into which the separated fluid is collected.

18. The apparatus of claim 17 further comprising a pump evacuating the second section of the chamber.

19. The apparatus of claim 18, wherein the pump is an ion pump.

20. The apparatus of claim 11, wherein the permeable membrane comprises a plurality of permeable membranes, each such membrane having an affinity for one of (i) a different gas, and (ii) a different vapor.

21. A system apparatus for estimating a property of a fluid downhole comprising:
a downhole tool including a filter having a permeable membrane and a porous filter to separate at least one of gas and vapor to form a separated fluid; and
a processor analyzing the separated fluid downhole to estimate the property of the separated fluid.

22. The system of claim 21, further comprising a rigid support for the filter.

23. The system of claim 21, further comprising:
a mass spectrometer exposed to the separated fluid; and
wherein the processor estimates the property of the separated fluid by observing a response from the mass spectrometer.

24. The system of claim 23, wherein the response is one of (i) an intensity of a charge to mass ratio; and (ii) a portion of a fragmentation pattern.

25. The system of claim 21, further comprising a valve that controls passage of the fluid through the filter.

26. The system of claim 21, wherein the permeable membrane comprises a plurality of permeable membranes, each such membrane having a thickness selected to allow passage of a selected fluid therethrough.

27. The system of claim 21 further comprising a chamber having a first section retrieving the fluid downhole, and a second section into which the separated fluid is collected.

28. The system of claim 27 further comprising a pump evacuating the second section of the chamber.

29. The system of claim 28, wherein the pump is an ion pump.

30. The system of claim 21, wherein the permeable membrane comprises a plurality of permeable membranes, each such membrane having an affinity for one of (i) a different gas, and (ii) a different vapor.

* * * * *